United States Patent [19] [11] 4,163,758
Kondo et al. [45] Aug. 7, 1979

[54] 2-NITROETHYLCYCLOPENTANE COMPOUNDS AND PROCESS FOR PREPARING THE SAME

[75] Inventors: Kiyosi Kondo, Yamato; Daiei Tunemoto; Teruo Umemoto, both of Sagamihara, all of Japan

[73] Assignee: Sagami Chemical Research Center, Tokyo, Japan

[21] Appl. No.: 939,937

[22] Filed: Sep. 6, 1978

[30] Foreign Application Priority Data

Sep. 9, 1977 [JP] Japan .............................. 52-107863
Feb. 8, 1978 [JP] Japan .................................. 53-12327

[51] Int. Cl.² ............................................ C07C 49/46
[52] U.S. Cl. ............................ 260/586 R; 260/590 C; 568/583; 568/586; 260/345.9 P; 260/448.8 R; 560/84; 560/193; 560/231; 568/838; 568/807
[58] Field of Search ........... 260/586 R, 590 C, 611 A, 260/611 B, 345.9, 448.8 R; 568/807, 838; 560/106, 84, 193, 231

[56] References Cited
U.S. PATENT DOCUMENTS 4,107,181   8/1978   Evans .................................... 568/807

OTHER PUBLICATIONS

Corey et al., J. Amer. Chem. Soc., 91, 5675 (1969).

Primary Examiner—Gerald A. Schwartz
Attorney, Agent, or Firm—Sughrue, Rothwell, Mion, Zinn and Macpeak

[57] ABSTRACT

2-Nitroethylcyclopentane compounds represented by the formula (I)

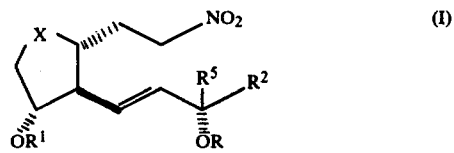

wherein X represents a

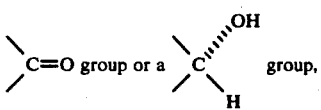

R and R¹ each represents a hydrogen atom or a protective group for a hydroxy group, R² represents an unsubstituted or substituted alkyl group having 1 to 8 carbon atoms and R⁵ represents a hydrogen atom or an alkyl group havng 1 to 4 carbon atoms, which are useful as intermediates for the synthesis of prostaglandin compounds, and a process for preparing the 2-nitroethylcyclopentane compounds of the formula (I).

3 Claims, No Drawings

2-NITROETHYLCYCLOPENTANE COMPOUNDS AND PROCESS FOR PREPARING THE SAME

BACKGROUND OF THE INVENTION

1. Field of the Invention

This invention relates to novel 2-nitroethylcyclopentane compounds having the formula (I) which are useful as intermediates for the synthesis of prostaglandin compounds.

2. Description of the Prior Art

It is well known that the naturally-occurring prostaglandin compounds are composed of 20 carbon atoms and contains in their structure a cyclopentanone ring and exist broadly in the brain, lung, kidney, semen, uterus membrane, etc. of living body. These prostaglandin compounds are also known to have a wide variety of excellent pharmacological activities such as anti-ulcer, hypotensive, anti-asthmatic, uterotonic activities depending upon critical differences in the chemical structure of the prostaglandin compounds, and recently the synthesis of prostaglandin compounds has been extensively studied.

Hitherto, in the synthesis of prostaglandin derivatives, the basic cyclopentanone structure is typically formed by (1) a method utilizing Dieckmann reaction as described, for example, in P. S. Pinkney, Org. Synthesis, Coll. Voll., 2, 116 (1943), (2) a method by Claisen condensation of 1,4-dicarbonyl compounds as described, for example, in R. A. Ellison, Synthesis, 397 (1973), (3) a method starting with cyclopentadiene as described, for example, in E. J. Corey et al., J. Amer. Chem. Soc. 93, 1489 (1971), (4) a method by ring-contracting procedure of cyclohexane derivatives as described, for example, in R. B. Woodward et al., J. Amer. Chem. Soc., 95, 6853 (1973) and (5) a method using a bicyclo[3.1.0]hexane compound as an intermediate as described, for example, in W. P. Schneider, Chem. Commun., 304 (1969) and E. J. Corey et al., J. Amer. Chem. Soc., 94, 4014 (1972).

Recently, various improved methods for the synthesis of prostaglandin compounds have been developed as described, for example, in G. Stork et al., J. Amer. Chem. Soc., 98, 1583 (1976) for the above method (1), and F. Johnson et al., J. Amer. Chem. Soc., 98, 1285 (1976) for the above method (2), but each of these conventional methods is not considered advantageous procedure from the standpoint of that it requires expensive and/or dangerous reagents, critical reaction conditions which are very difficult to control, and isolation and purification of the desired product with considerable difficulty, and that the method generally has low selectivity of reaction thereby resulting in low yield of the desired product.

Also, it is well known that lactol derivatives are very useful starting materials for the synthesis of prostaglandin compounds, as described in E. J. Corey et al., J. Amer. Chem. Soc., 91, 5675 (1969). The 2-nitroethylcyclopentane compounds of the formula (I) of the present invention can be converted into the above lactol derivatives by, for example, converting the nitroethyl moiety of the compounds into an aldehyde group, as described hereinafter.

Hitherto, various methods for preparing lactol derivatives or precursors therefor have been proposed. Typical examples of such methods are (1) a method starting with an adduct of cyclopentadiene obtained by Diels-Alder reaction, as described in E. J. Corey et al., J. Amer. Chem. Soc., 91, 5657 (1969), E. D. Brown et al., Chem. Commun., 642 (1974), and G. Jones et al., Chem. Commun., 609 (1972); 2) a method utilizing a ring-opening reaction of an epoxide derived from 1,4-dihydroxy-2-cyclopentene, as described in J. Fried et al., J. Amer. Chem. Soc., 94, 4343 (1972); (3) a method starting with dicyclopentadiene, as described in D. Brewster et al., Chem. Commun., 1235 (1972); (4) a method comprising solvolysis of a cyclopropane derivative, as described in, for example, R. C. Kelly et al., J. Amer. Chem. Soc., 95, 2746 (1973); (5) a method starting with cis-1,3,5-cyclohexanetriol, as described in R. B. Woodward et al., J. Amer. Chem. Soc., 95, 6853 (1973); (6) a method utilizing a ring-contracting reaction of a cyclohexene derivative, as described in E. J. Corey et al., Tetrahedron Lett., 3091 (1973); (7) a method starting with an adduct obtained by the Prins reaction between norbornadiene and formaldehyde or chloral, as described in R. Peel et al., Chem. Commun., 151 (1974) and S. Takano et al., J. Org. Chem., 42, 786 (1977), etc.

Each of these conventional methods has characteristic features, but generally, also has one or more disadvantages in that these methods comprises a number of reaction steps, require expensive or dangerous reagents and exhibit low steric selectivity and, therefore, appear to be unsatisfactory as industrial methods.

DETAILED DESCRIPTION OF THE INVENTION

As a result of extensive studies on a process for effectively producing prostaglandin analogues and prostaglandin compounds, it was found that novel 2-nitroethylcyclopentane compounds of the formula (I) can be easily converted into lactol compounds which are useful precursors for the prostaglandin compounds and that these 2-nitroethylcyclpentane compounds can be efficiently prepared in accordance with the process of this invention.

The present invention is therefore to provide novel 2-nitroethylcyclopentane compounds represented by the formula (I) wherein X represents a

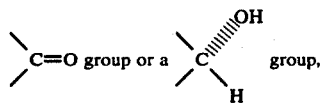

R and $R^1$ each represents a hydrogen atom or a protective group for a hydroxy group, $R^2$ represents an unsubstituted or substituted alkyl group having 1 to 8 carbon atoms and $R^5$ represents a hydrogen atom or an alkyl group having 1 to 4 carbon atoms; and a process for preparing the same.

The characteristic features of the 2-nitroethylcyclopentane compounds of the formula (I) reside in that these compounds possess all the functional groups required for prostaglandin compounds and, in addition, these functional groups have the steric configuration required for the synthesis of naturally-occurring prostaglandins. In particular, the nitroethyl side chain can be converted into a different functional group, thereby making it possible to synthesize an α-side chain of prostaglandin. Thus, the 2-nitroethylcyclopentane compounds of the formula (I) are considered very useful intermediates for the synthesis of prostaglandin compounds.

The term "an alkyl group having 1 to 4 carbon atoms" as used herein means a straight or branched chain alkyl group having 1 to 4 carbon atoms and includes, for example, a methyl, ethyl, propyl, isopropyl, n-butyl, sec-butyl or tert-butyl group.

The term "an unsubstituted or substituted alkyl group having 1 to 8 carbon atoms" as used herein means a straight or branched chain alkyl group having 1 to 8 carbon atoms and includes, in addition to the examples of the alkyl group having 1 to 4 carbon atoms given above, a pentyl, hexyl, heptyl or octyl group which may be substituted with an —O—alkyl group or an —S—alkyl group wherein the alkyl moiety can be a straight or branched chain and has 1 to 4 carbon atoms, or a phenoxy group which may be substituted with a halogen atom or an alkyl group having 1 to 4 carbon atoms.

The term "an aryl group" as used herein means an unsubstituted or substituted phenyl group wherein the substituent is a halogen atom, an alkyl or alkoxy group having 1 to 4 carbon atoms.

The term "halogen" as used herein means fluorine, chlorine, bromine and iodine.

The term "a protective group for a hydroxy group" as used herein refers to protective groups which are generally used for protecting a hydroxy group and which are well known in the art. Typical examples of such protective groups are a tetrahydropyranyl group, a tri(lower alkyl)silyl group, a benzyl group, an alpha-lower alkoxy-lower alkyl group, a lower alkanoyl group, a benzoyl group, etc.

The 2-nitroethylcyclopropane compounds of the formula (I) can be prepared in accordance with the reaction scheme shown below.

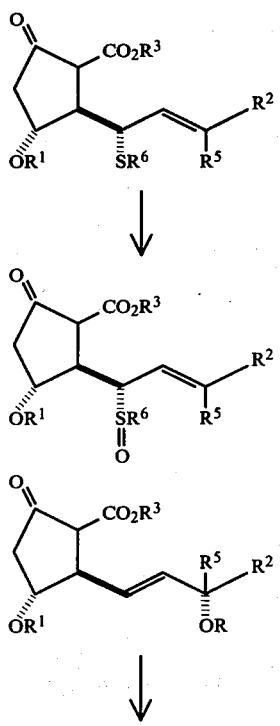

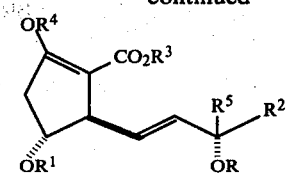

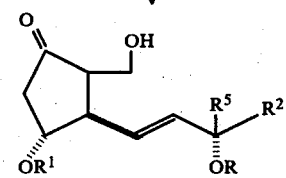

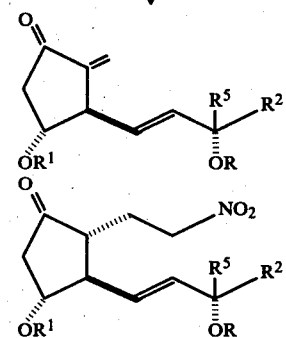

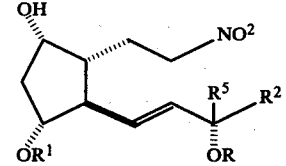

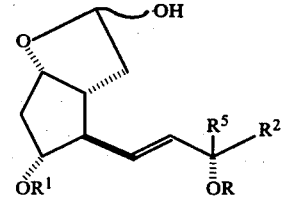

wherein R, $R^1$, $R^2$ and $R^5$ are as defined above, and $R^4$ represents an alkyl group having 1 to 4 carbon atoms or a tri(lower alkyl)silyl group, and $R^6$ represents a straight or branched chain alkyl group having 1 to 4 carbon atoms or an unsubstituted or substituted phenyl group, and $R^3$ represents an alkyl group having 1 to 4 carbon atoms.

The process of this invention is further illustrated below in greater detail.

The first step of the process comprises oxidation of the cyclopentanone compound of the formula (VII) to produce the compound of the formula (VI). This oxidation can be achieved by using an oxidizing agent in an inert solvent at a temperature of about −80° C. to about 100° C., preferably at room temperature for a period of about 1 to about 24 hours.

Suitable examples of oxidizing agents which can be used for the above oxidation are inorganic oxidizing agents such as sodium iodate, hydrogen peroxide, oxygen, ozone, manganese dioxide, selenium dioxide, chromic acid, nitric acid, dinitrogen tetraoxide and the like, and organic oxidizing agents such as peracetic acid, perbenzoic acid, m-chloroperbenzoic acid, iodosobenzene and the like. Preferred organic oxidizing agents are organic peroxides described above, more preferably, m-chloroperbenzoic acid, since these peroxides do not adversely affect reactive groups present in the cyclopentanone sulfide compounds of the formula (VII), such as a carbonyl group and an ester group. The oxidizing agent can be used in an approximately equimolar amount relative to the compound of the formula (VII).

Suitable examples of the inert solvents are water, alcohols such as methanol, ethanol and the like, ethers such as diethyl ether, tetrahydrofuran, dimethoxyethane and the like, but other inert solvents which do not take part in the oxidation can be used as well.

The starting materials having the formula (VII) used in the process of this invention can be prepared as described in the applicants' co-pending U.S. Patent Application Ser. No. 862,329 filed Dec. 20, 1977 (British Patent Application No. 7045/77, West German Patent Application No. P 27 08 220.8 or French Patent Application No. 77.05665, i.e., by reacting an acetoacetic acid ester with an unsaturated aldehyde, protecting an alcohol moiety of the resulting addition product, diazotizing the resulting compound followed by subjecting the compound to carbene or carbenoid formation and ring-opening addition reaction of the resulting bicyclic compound with a mercaptan compound.

The compound of the formula (VI) thus obtained can be converted into the corresponding 3α-(3α-hydroxy-trans-1-alkenyl)-4-oxycyclopentanone-2-carboxylic acid ester by treating the compound of the formula (VI) with a reagent having "thiophilicity", i.e., a reagent having a high affinity for a sulfur atom, for example, organic amines such as triethylamine, diethylamine, pyridine and the like, organophosphorus compounds such as trimethyl phosphite, triethyl phosphite, tris-dimethylaminophosphine and the like, and mercaptans, in an approximately equimolar amount relative to the compound of the formula (VI) at a temperature of from about −30° C. to room temperature for a period of about 2 to about 24 hours in an inert solvent, e.g., alcohols such as methanol, ethanol, t-butanol and the like, ethers such as diethyl ether, tetrahydrofuran and the like, dimethyl sulfoxide, hexamethylphosphoric triamide and the like, whereby the compound of the formula (V) wherein R represents a hydrogen atom can be obtained. The compound of the formula (V) wherein R represents a protective group can be prepared by treating the above hydroxy compound with vinyl ethers such as dihydropyrane, ethylvinyl ether in the presence of an acid catalyst or by treating the above hydroxy compound with halides such as trialkylsilyl halides, benzyl halides, alkanoyl halides, etc. in the presence of a base.

Suitable examples of protective groups for the hydroxy group are a tetrahydropyranyl group, a 1-ethoxyethyloxy group, or a 1-methyl-1-ethoxyethyloxy group.

The compound of the formula (IV) can be prepared from the above prepared 4-oxy-2,3-disubstituted cyclopentanone compound of the formula (V) by protecting the carbonyl group contained in the compound of the formula (V) with a protective group for a hydroxy group which is well known in the art.

The protection of the carbonyl group can be achieved by the following procedures.

(a) The carbonyl group can be protected by the reaction of the compound of the formula (V) with a diazoalkane having 1 to 4 carbon atoms, for example, diazomethane, diazoethane, diazobutane and the like. Such diazoalkane can be used in an amount of from about 1 to about 3 mols, preferably an equimolar amount relative to the compound of the formula (V). The reaction between the cyclopentanone compound (V) and a diazoalkane can be advantageously effected at a temperature of about 0° to about 20° C., preferably at room temperature for about 1 to about 24 hours, in a solvent such as ethers, for example, diethyl ether, tetrahydrofuran and the like, methylene chloride, or a mixture thereof.

(b) The carbonyl group can be protected by the reaction of the compound of the formula (V) with a silylating agent which is capable of introducing a silyl group as a protective group. This silylation reaction can be advantageously achieved using a trialkylchlorosilane such as trimethylchlorosilane, dimethyl i-propylchlorosilane, dimethyl t-butylchlorosilane and the like in an approximately equimolar amount relative to the compound of the formula (V), in the presence of a base.

Suitable examples of bases which can be used in the silylation reaction are organic amines such as ethylamine, diethylamine, triethylamine, isopropylamine, n-butylamine, tri-n-butylamine, cyclohexylamine, dimethylaniline, pyrrolidine, piperidine, morpholine, pyridine, quinoline and the like. These organic amines can be used in an approximately equimolar amount relative to the compound of the formula (V). Alternatively, the above silylation reaction can be attained by treating the compound of the formula (V) with a silylating agent such as hexamethyldisilazane, bistrimethylsilylacetamide and the like. These silylating agents can be used in an amount of about 1 to about 2 mols, preferably 1 to 1.1 mol, per mol of the compound of the formula (V).

In either case, the silylation reaction can be preferably conducted in a solvent, for example, ethers such as diethyl ether, tetrahydrofuran, dioxane, dimethyl ether and the like, amides such as dimethylformamide, dimethylacetamide, hexamethylphosphoric triamide and the like, nitriles such as acetonitrile and the like, sulfoxides such as dimethyl sulfoxide and the like, or a mixture thereof. The silylation reaction can be carried out at a temperature of from about −30° C. to about 40° C., preferably at room temperature for a periof of about 10 minutes to about 24 hours.

The compounds of the formula (III), 2-hydroxymethyl-4-oxycyclopentanone compounds, can then be prepared from the enol ether compounds of the formula (IV) obtained as described above by reduction, followed by hydrolysis. This reduction can be effected using a metal hydride, in particular, a complex metal hydride, as a reducing agent in an amount of about 1 to about 5 mols, preferably an equimolar amount relative to the enol ether compound of the formula (IV).

Suitable examples of reducing agents are lithium aluminum hydride, lithium alkoxy aluminum hydrides or sodium alkoxy aluminum hydrides such as lithium tri-tert-butoxy aluminum hydride and the like, and dialkyl aluminum hydrides such as diisobutyl aluminum hydride.

The reduction can be advantageously conducted in a solvent, for example, ethers such as diethyl ether, 1,2-dimethoxyethane, tetrahydrofuran and the like, or hydrocarbons such as benzene, toluene, xylene, hexane and the like, or a mixture thereof, at a temperature of from about −80° C. to room temperature.

The subsequent hydrolysis of the resulting reaction mixture obtained from the reduction can be achieved using, optionally, an acid catalyst. However, when the protective group ($R^4$) in the formula (IV) is a silyl group, this protective group can be removed by mere water washing procedure and, therefore, no specific procedure is required for the removal of the silyl group to obtain the corresponding 2-hydroxymethyl compound of the formula (III). When the protective group ($R^4$) is an alkyl group, the compound of the formula (IV) can be subjected to hydrolysis using an acid catalyst thereby yielding 2-hydroxymethyl-3,4-disubstituted cyclopentanone compound of the formula (III).

Suitable examples of acid catalysts which can be used in the hydrolysis are sulfonic acids such as p-toluenesulfonic acid, methanesulfonic acid and the like, inorganic acids such as hydrochloric acid, sulfuric acid, perchloric acid and the like, ammonium chloride and the like. These acid catalysts can be used in a catalytic amount.

Suitable examples of solvents which can be used in the above hydrolysis are water, alcohols such as methanol, ethanol and the like, ethers such as diethyl ether, 1,2-diethoxyethane, tetrahydrofuran and the like, hydrocarbons such as benzene, toluene, xylene and the like, or a mixture thereof.

The hydrolysis can be carried out at a temperature of about −40° C. to room temperature for about 1 to about 24 hours.

The 2-methylene-4-oxycyclopentanone compounds of the formula (II) can then be prepared from the corresponding 2-hydroxymethyl compounds of the formula (III) by treating the 2-methylhydroxy compound with a sulfonic acid compound in the presence of a base.

Suitable examples of sulfonic acid compounds are halides or anhydrides of methanesulfonic acid, ethanesulfonic acid, p-toluenesulfonic acid and the like. These sulfonic acid compounds can be used in an approximately equimolar amount relative to the compound of the formula (III).

Examples of bases which can be used in the above treatment with a sulfonic acid compound are ethylamine, diethylamine, triethylamine, i-propylamine, n-butylamine, tri-n-butylamine, dimethylaniline, pyrrolidine, piperidine, morpholine, pyridine and the like. These bases can be used in an excess amount so as to serve as solvents, but ehters such as diethyl ether, 1,2-dimethoxyethane, tetrahydrofuran and the like, amides such as dimethylformamide, dimethylacetamide, hexamethylphosphoric triamide and the like, nitriles such as acetonitrile and the like, sulfoxides such as dimethyl sulfoxide and the like can be used as solvents.

The reaction between the 2-hydroxymethyl compound of the formula (III) and a sulfonic acid compound can be carried out at a temperature of about −30° C. to about 40° C. for a period of from about 1 to about 24 hours, depending upon the reactivity of the sulfonic acid compound used. The reaction is preferably carried out at room temperature from the standpoint of ease in operation.

The final step of the process in accordance with the present invention comprises reacting the thus obtained α-methylenecyclopentanone compound of the formula (II) with nitromethane in the presence of a base to produce a compound of the formula (I) wherein X represents a >C=O group [Compound of the formula (Ia)] and then selectively reducing the carbonyl group of the compound of the formula (Ia) without affecting the nitro group present in the α-side chain of the compound of the formula (Ia) to produce a compound of the formula (I) wherein X represents a

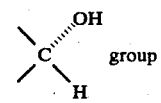

group

[Compound of the formula (Ib)].

Examples of bases which can be used in the reaction between the compound of the formula (II) with nitromethane are alkali metal hydroxides such as sodium hydroxide, potassium hydroxide and the like, alkali metal alkoxides such as sodium methoxide, potassium ethoxide and the like, alkali metal hydrides such as sodium hydride, potassium hydride and the like, alkali metal carbonates such as sodium carbonate, potassium carbonate and the like, amines such as ethylamine, diethylamine, triethylamine, isopropylamine, n-butylamine, tri-n-butylamine, cyclohexylamine, dimethylaniline, pyrrolidine, piperidine, morpholine, pyridine, 1,1,3,3,-tetramethylguanide, quinoline and the like, and ammonium salts such as methyl triethylammonium hydroxide, benzyl trimethylammonium hydroxide (Triton B) or the methoxide thereof, etc.

A catalytic amount of these bases is generally sufficient.

In carrying out the reaction, a solvent is preferably used, and suitable examples of solvents are alcohols such as methanol, ethanol and the like, ethers such as diethyl ether, 1,2-dimethoxyethane, tetrahydrofuran and the like, hydrocarbons such as benzene, toluene, hexane and the like, or a mixture of these solvents. Generally, nitromethane is used in an equimolar amount relative to the compound of the formula (II), but can be used in a molar excess so as to serve as both the reactant and a solvent. The reaction generally proceeds smoothly at room temperature (about 15° to about 30° C.) without using any specific heating or cooling means and is completed within a period of about 1 to about 3 hours.

Generally, β-hydroxy-substituted cyclopentanone compounds are known to be unstable under basic or acidic conditions and under such conditions tend to be converted into cyclopentenone compounds. However, in accordance with the process of this invention, the above side reaction leading to the cyclopentenone compounds is inhibited thereby yielding the desired 2-nitromethane compounds (Ia) in high yield. Further, as one of the characteristic features of the process of this invention, only a cyclopentane compound having the most stable steric configuration of the formula (Ia) can be obtained selectively due to thermodynamic influences since the reaction between nitromethane and the compound of the formula (II) is carried out under a basic condition.

The compounds of the formula (Ib) can then be obtained from the compound of the formula (Ia) by selectively reducing the carbonyl group with a reducing agent without affecting the nitro group contained in the compound of the formula (Ia).

Examples of reducing agents are selective reducing agents such as lithium limonenyltexyl borohydride, lithium perhydro-9b-boraphenalylhydride, lithium tris-(t-butyl)borohydride, a potassium trialkyl borohydride and the like. These selective reducing agents can be used in an amount of about 1 to about 2 mols.

The reduction reaction can be preferably conducted in a solvent, for example, diethyl ether, 1,2-dimethoxyethane, tetrahydrofuran and the like, hydrocarbons such as benzene, toluene, xylene, hexane and the like, or a mixture thereof, at a temperature of about $-80°$ C. to room temperature for a period of about 0.5 to about 1 hour.

The 2-nitroethylcyclopentane compounds of the formula (Ib) thus obtained can be converted in high yield into the well known lactol compounds of the formula (XII) described previously. A typical procedure for the above conversion comprises reduction of the compound of the formula (Ib) with titanium trichloride, oxidation with potassium permanganate, oxone, t-butyl hypohalide and the like under basic conditions, or Nef reaction using a base and an acid.

The present invention is further illustrated in greater detail by the followng Reference Example and Examples, but they are given for illustrative purposes only and are not to be construed as limiting the present invention. Unless otherwise indicated, all parts, percents and ratios are by weight.

REFERENCE EXAMPLE 1

1.0 g of a mixture of methyl exo-6-(trans-1-heptenyl)-exo-4-(1-ethoxyethoxy)-2-oxobicyclo[3.1.0]hexane-1-carboxylate and methyl exo-6-(trans-1-heptenyl)-endo-4-(1-ethoxyethoxy)-2-oxobicyclo[3.1.0]hexane-1-carboxylate (about 2:1 ratio) was dissolved in 16 ml of t-butanol-water (4:1 by volume), and 0.37 g. of thiophenol was added to the solution in an argon atmosphere while cooling in an ice bath with vigorous stirring. A catalytic amount of triethylamine was added to the mixture, followed by stirring for 20 minutes. After completion of the reaction, a saturated aqueous solution of ammonium chloride was added to the reaction mixture which was then allowed to warm to room temperature. The mixture was extracted with ethyl acetate and the extract was washed with water. The solvent was distilled off and the resulting residue was purified by silica gel column chromatography eluting with ethyl acetate-n-hexane to obtain 0.74 g of methyl $2\beta$-(1$\alpha$-phenylthio-trans-2-octenyl)-3$\alpha$-(1-ethoxyethyloxy)-5-oxocyclopentane-1-carboxylate in a yield of 56% and in a conversion yield of 83%, together with 0.33 g of the unreacted methyl exo-6-(trans-1-heptenyl)-endo-4-(1-ethoxyethoxy)-2-oxobicyclo[3.1.0]hexane-1-carboxylate.

NMR(CCl$_4$) $\delta$: 0.7–1.5 (m, 15H), 1.9 (m, 2H), 2.1–2.9 (m, 2H), 2.9–3.2 (m, 2H), 3.3–3.9 (m, 6H), 4.0–4.3 (m, 1H), 4.5–4.8 (m, 1H), 5.2–5.5 (m, 1H), 7.0–7.4 (m, 5H).

Infrared Absorption Spectrum (neat): 1766, 1738, 1666, 1625, 1588, 1440, 1255, 1132, 1090, 1056, 750, 693 cm$^{-1}$.

Elementary Analysis: Calc'd for C$_{25}$H$_{36}$O$_5$S: C, 66.93; H, 8.09%. Found: C, 67.00, H, 8.07%.

EXAMPLE 1

300 mg (0.67 mmol) of methyl $2\beta$-(1$\alpha$-phenylthio-trans-2-octenyl)-3$\alpha$-(1-ethoxyethyloxy)-5-oxocyclopentane-1-carboxylate obtained in Reference Example 1 was dissolved in 10 ml of absolute methanol and, after cooling to $-30°$ C., a solution of 165 mg (0.80 mmol) of m-chloroperbenzoic acid in 7 ml of absolute methanol was added dropwise to the above solution over a period of about 10 minutes while stirring in an argon atmosphere. After completion of the addition, the mixture was stirred for 2 hours and a solution of 420 mg of trimethyl phosphite dissolved in 3 ml of absolute methanol was added thereto. The temperature of the resulting reaction system was then allowed slowly to elevate to 5° to 10° C. and allowed to stand overnight at that temperature. The solvent was distilled off, and the resulting residue was purified by silica gel column chromatography eluting with ethyl acetate-n-hexane (2:3 by volume) to obtain 0.23 g (97% yield) of methyl $2\beta$-(3$\alpha$-hydroxy-trans-1-octenyl)-3$\alpha$-(1-ethoxyethyloxy)-5-oxocyclopentane-1-carboxylate.

NMR (CCl$_4$) $\delta$: 0.7–1.8 (m, 17H), 2.1–2.8 (m, 2H), 2.9–3.8 (m, 7H), 3.8–4.1 (m, 2H), 4.5–4.8 (m, 1H), 5.3–5.6 (m, 2H).

EXAMPLE 2

0.23 g of methyl $2\beta$-(3$\alpha$-hydroxy-trans-1-octenyl)-3$\alpha$-(1-ethoxyethyloxy)-5-oxocyclopentane-1-carboxylate was dissolved in 1 ml of anhydrous diethyl ether and 1 ml of ethyl vinyl ether was added thereto. The mixture was then allowed to react overnight while cooling in an ice bath in the presence of a catalytic amount of POCl$_3$. After adding several drops of triethylamine to the mixture, the solvent was distilled off and the residue was purified by silica gel column chromatography using ethyl acetate-n-hexane as an eluant to obtain 0.225 g (81% yield) of methyl $2\beta$-[3$\alpha$-(1-ethoxyethyloxy)-trans-1-octenyl]-3$\alpha$-(1-ethoxyethyloxy)-5-oxocyclopentane-1-carboxylate.

Elementary Analysis: Calc'd for C$_{23}$H$_{40}$O$_7$: C, 64.46; H, 9.41%. Found: C, 64.60; H, 9.24%.

NMR (CCl$_4$)$\delta$: 0.7–1.8 (m, 23H), 2.1–2.9 (m, 2H), 2.9–3.7 (m, 9H), 3.7–4.1 (m, 2H), 4.4–4.8 (m, 2H), 5.3–5.6 (m, 2H).

EXAMPLE 3

100 mg of methyl $2\beta$-[3$\alpha$-(1-ethoxyethyloxy)-trans-1-octenyl]-3$\alpha$-(1-ethoxyethyloxy)-5-oxocyclopentane-1-carboxyalte was dissolved in 1.5 ml of anhydrous diethyl ether and 0.3 ml of bistrimethyl silylacetamide in an argon atmosphere while cooling in an ice bath and stirring, followed by stirring at that temperature for 2 hours then stirring at room temperature for 1.5 hours. After completion of the reaction, the reaction mixture was concentrated under reduced pressure to obtain methyl $2\beta$-[3$\alpha$-(1-ethoxyethyloxy)-trans-1-octenyl]-3$\alpha$-(1-ethoxyethyloxy)-5-trimethylsilyloxy-5-cyclopentene-1-carboxylate as a yellow oily substance in a quantitative yield.

EXAMPLE 4

The crude compound prepared as described in Example 3 above was dissolved in 2 ml of anhydrous toluene and the solution was cooled to $-78°$ C. 1 ml of a solution of diisobutylaluminum hydride in n-hexane (25 g of the hydride dissolved in 100 ml of hexane) was added dropwise to the above solution while stirring in an argon atmosphere. After stirring the mixture for 20 minutes, a small amount of methanol was added to the mixture which was then allowed to warm to room temperature. The precipitate formed is removed by filtration, and the filtrate was washed successively with ethyl acetate and water and dried over anhydrous magnesium sulfate. The solvent was then ditilled off to obtain 2-hydroxymethyl-3β-[3α-(1-ethoxyethyloxy)-trans-1-octenyl]-4α-(1-ethoxyethyloxy)cyclopentanon-1-one as a yellow oily substance.

EXAMPLE 5

The crude compound prepared as described in Example 4 above was dissolved in 2 ml of anhydrous pyridine, and 0.05 ml of methanesulfonic acid chloride was added to the solution followed by stirring for 2 hours. After completion of the reaction, ice-water was added to the mixture, and the mixture was extracted with ethyl acetate. The extract was washed with water and dried over anhydrous magnesium sulfate. The solvent was then distilled off and the resulting oily substance was dissolved in 2 ml of anhydrous tetrahydrofuran. 0.03 ml of triethylamine was added to the solution while cooling in an ice bath and the mixture was stirred for 1 hour. The solvent was distilled off, and the residue was purified by silica gel column chromatography using ethyl acetate-n-hexane as an eluant to obtain 81 mg of 2-methylene-3β-[3α-(1-ethoxyethyloxy)-trans-1-octenyl]-4α-(1-ethoxyethyloxy)cyclopentane-1-one. The overall yield of the above compound from the compound of the formula (V), i.e., methyl 2β-[3α-(1-ethoxyethyloxy)-trans-1-octenyl]-3α-(1-ethoxyethyloxy)-5-oxocyclopentane-1-carboxylate, was 91%.

Elementary Analysis: Calc'd for $C_{22}H_{38}O_5$: C, 69.08; H, 10.01%. Found: C, 69.03; H, 10.12%.

NMR $(CCl_4)\delta$: 0.7–1.8 (m, 23H), 2.19 (dd, J=18, 8Hz, ½H), 2.27 (dd, J=18, 8Hz, ½H), 2.58 (dd, J=18, 6.5Hz, 0.5H), 2.60 (dd, J=18, 6.5Hz, 0.5H), 3.1–37 (m, 5H), 3.9 (bm, 1H), 3.94 (bq, J=7Hz, 1H), 4.5–4.8 (m, 2H), 5.06 (m, 1H), 5.45 (m, 2H, 5.95 (m, 1H).

Infrared Absorption Spectrum (neat): 1733, 1639, 1387, 1125, 1085, 1065 cm$^{-1}$.

EXAMPLE 6

1.60 g (3.74 mmol) of methyl 2β-[3α-(1-ethoxythyloxy)-trans-1-octenyl]-3α-(1-ethoxyetholoxy)-5-oxocyclopentane-1-carboxylate was dissolved in 25 ml of anhydrous diethyl ether, and 2.0 ml of bistrimethylsilylacetamide was added thereto in an argon atmosphere while cooling in an ice bath and stirring. The mixture was then stirred for 2 hours and further stirred at room temperature for 1.5 hour. After completion of the reaction, the reaction mixture was concentrated under reduced pressure to obtain a corresponding trimethylsilyl enol ether as a yellow oily substance in a quantitative yield. The enol ether thus obtained was dissolved in 30 ml of anhydrous toluene and the solution was cooled to −78° C. 6.4 ml of a solution of diisobutylaluminum hydride in n-hexane (25 g of the hydride dissolved in 100 ml n-hexane) was added dropwise to the above solution while stirring in an argon atmosphere. After stirring for 20 minutes, 3 ml of methanol, 20 ml of ethyl acetate and 20 ml of water were added to the mixture, and the temperature of the mixture was then elevated to room temperature. The precipitate formed was removed by filtration, and the filtrate was extracted with ethyl acetate. The extract was washed with an aqueous sodium chloride solution and dried over anhydrous magnesium sulfate. After filtration, the filtrate was concentrated, and the resulting viscous oily residue was dissolved in 10 ml of anhydrous pyridine. 643 mg (5.6 mmol) of methanesulfonic acid chloride was added to the solution while cooling in an ice bath, followed by stirring for 2 hours. Ice water was added to the mixture which was then extracted with ethyl acetate. The extract was washed with an aqueous solution of sodium chloride and dried over anhydrous magnesium sulfate. The solvent was distilled off, and the resulting oily substance was dissolved in 20 ml of anhydrous tetrahydrofuran, and a solution of triethylamine (0.378 g, 3.74 mmol of triethylamine dissolved in 3 ml of tetrahydrofuran) was added while cooling in an ice bath, followed by stirring for one hour. Thereafter, an aqueous solution of ammonium chloride was added to the mixture and ethyl acetate was added to the mixture to separate layers. The ethyl acetate layer was washed with a saturated aqueous solution of sodium chloride and dried over anhydrous magnesium sulfate. The solvent was distilled off and the residue was purified by silica gel column chromatography eluting with ethyl acetate-n-hexane (3:7 by volume) to obtain 1.07 g (75% yield) of 2-methylene-3β-[3α-(1-ethoxyethyloxy)-trans-1-octenyl]-4α-(1-ethoxyethyloxy)cyclopentan-1-one.

EXAMPLE 7

1.5 ml of tetrahydrofuran and 3 ml of nitromethane was added to 15 mg of sodium hydride (50% oil) in an argon atmosphere with stirring. After 10 minutes, a solution of 100 mg (0.26 mmol) of 2-methylene-3β-[3α-(1-ethoxyethyloxy)-trans-1-octenyl]-4α-(1-ethoxyethyloxy)cyclopentane-1-one dissolved in 2 ml of tetrahydrofuran was added to the mixture. After stirring for one hour at room temperature, an aqueous ammonium chloride solution was added thereto and the mixture was extracted with ethyl acetate. The organic layer was washed with an aqueous sodium chloride solution and dried over anhydrous magnesium sulfate. After filtration, the filtrate was concentrated, and the resulting residue was purified by silica gel column chromatography to obtain 92 mg (79% yield) of 2α-(2-nitroethyl)-3β-[3α-(1-ethoxyethyloxy)-trans-1-octenyl]-4α-(1-ethoxyethyloxy)-cyclopentan-1-one.

Infrared Absorption Spectrum: 2925, 1742, 1553, 1445, 1380, 1340, 1130, 1080, 1060, 1030, 970, 950, 930, 885, 845 cm$^{-1}$.

Elementary Analysis: Calc'd for $C_{23}H_{41}NO_7$: C, 62.28; H, 9.31; N, 3.16%. Found: C, 62.39; H, 9.41; N, 2.98%.

EXAMPLE 8

820 mg of 2α-(2-nitroethyl)-3β-[3α-(1-ethoxyethyloxy)-trans-1-octenyl]-4α-(1-ethoxyethyloxy)cyclopentan-1-one was dissolved in 20 ml of tetrahydrofuran. 10 ml of a 0.5 M tris(sec-butyl)-potassium borohydride solution in tetrahydrofuran was added to the above solution while cooling to −75° C. and stirring. After stirring for 1.5 hour, the reaction mixture was decomposed with water and extracted with ethyl acetate. The organic layer was washed with an aqueous solution of sodium chloride and dried over anhydrous magnesium sulfate. After filtration, the filtrate was concentrated and the resulting residue was purified by silica gel column chromatography eluting with methyl acetate-n-hexane (2:3 by volume) to obtain 1α-hydroxy-2α-(2-nitroethyl)-3β-

[3α-(1-ethoxyethyloxy)-trans-1-octenyl]-4α-(1-ethoxyethyloxy)-cyclopentane in a quantitative yield.

Infrared Absorption Spectrum: 3400, 2925, 1555, 1460, 1380, 1340, 1260, 1210, 1130, 1080, 1055, 1030, 970, 955, 930 cm$^{-1}$.

Elementary Analysis: Calc'd for $C_{23}H_{43}NO_7$: C, 62.00; H, 9.73%. Found: C, 61.90; H, 9.77%.

EXAMPLE 9

200 mg (0.45 mmol) of 1α-hydroxy-2α-(2-nitroethyl)-3β-[3α-(1-ethoxyethyloxy)-trans-1-octenyl]-4α-(1-ethoxyethyloxy)cyclopentane was dissolved in 4 ml of methanol. A solution of 40 mg of sodium methoxide in 4 ml of methanol was prepared separately, and added to the above solution. After 5 minutes, 10 ml of an aqueous solution of titanium trichloride buffered with ammonium acetate prepared as described in J. Org. Chem., 38, 4367 (1973) was added to the mixture. After 40 minutes, ethyl acetate and an aqueous solution of sodium bicarbonate were added to the mixture, and the reaction mixture was filtered through Celite. The organic layer was separated, washed with an aqueous sodium chloride solution and dried over anhydrous magnesium sulfate. After filtration, the filtrate was concentrated and the residue was purified by silica gel column chromatography eluting with ethyl acetate-n-hexane (1:1 by volume) to obtain 150 mg (81% yield) of 2-oxa-3-hydroxy-6-syn-[3α-(1-ethoxyethyloxy)-trans-1-octenyl]-7-anti-(1-ethoxyethyloxy)-cis-bicyclo[3.3.0]octane.

Infrared Absorption Spectrum: 3400, 2925, 1445, 1380, 1340, 1130, 1090, 1060, 1030, 1010, 970, 955, 930, 880, 840, 810 cm$^{-1}$.

Elementary Analysis: Calc'd for $C_{23}H_{42}O_6$: C, 66.63; H, 10.21%. Found: C, 66.55; H, 10.31%.

What is claimed is:

1. A 2-nitroethylcyclopentane compound represented by the formula (I)

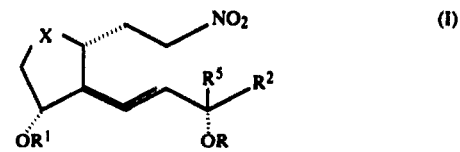

wherein X represents a

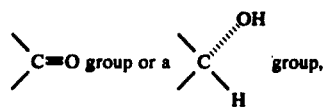

R and R$^1$ each represents a hydrogen atom or a conventional protective group for a hydroxy group, R$^2$ represents an unsubstituted or substituted alkyl group having 1 to 8 carbon atoms where the substituents are —O— alkyl of 1–4 carbon atoms, —S— alkyl of 1–4 carbon atoms, phenoxy optionally substituted with a halogen atom or an alkyl group having 1–4 carbon atoms and R$^5$ represents a hydrogen atom or an alkyl group having 1 to 4 carbon atoms.

2. 2α-(2-Nitroethyl)-3β-[3α-(1-ethoxyethyloxy)-trans-1-octenyl]-4-(1-ethoxyethyloxy)-cyclopentan-1-one, according to claim 1.

3. 1α-Hydroxy-2α-(2-nitroethyl)-3β-[3α-(1-ethoxyethyloxy)-trans-1-octenyl]-4α-(1-ethoxyethyloxy)-cyclopentane, according to claim 1.

* * * * *